United States Patent [19]

Taricco

[11] Patent Number: 5,666,878
[45] Date of Patent: Sep. 16, 1997

[54] WASTE DISPOSAL SYSTEM WHICH INCLUDES A VESSEL WITH AN OUTER COOLING JACKET

[75] Inventor: Todd Taricco, Zephyr Cove, Nev.

[73] Assignee: Dover Corporation, New York, N.Y.

[21] Appl. No.: 396,733

[22] Filed: Mar. 1, 1995

Related U.S. Application Data

[63] Continuation-in-part of Ser. No. 296,517, Aug. 26, 1994, abandoned.

[51] Int. Cl.⁶ .................................................. B30B 15/34
[52] U.S. Cl. ....................... 100/73; 100/90; 100/94; 100/250; 100/317; 100/316; 100/326; 241/39; 241/101.2; 241/606
[58] Field of Search ............... 100/73, 90, 92, 100/93 R, 93 P, 94, 250; 241/39, 101.2, 606

[56] References Cited

U.S. PATENT DOCUMENTS

| | | |
|---|---|---|
| 2,731,208 | 1/1956 | Dodd . |
| 3,383,228 | 5/1968 | Rekate et al. ............... 100/93 P |
| 3,547,577 | 12/1970 | Lovercheck . |
| 3,589,276 | 6/1971 | Swallert . |
| 3,653,871 | 4/1972 | Tempe . |
| 3,659,427 | 5/1972 | Harza ........................... 100/93 P |
| 3,685,309 | 8/1972 | Harza . |
| 3,691,648 | 9/1972 | Kraus . |
| 3,785,281 | 1/1974 | Ligh . |
| 3,808,766 | 5/1974 | Hutchinson et al. . |
| 3,821,927 | 7/1974 | Stratman et al. . |
| 3,831,514 | 8/1974 | Jernstrom . |
| 3,861,117 | 1/1975 | DeFilippi . |
| 3,926,107 | 12/1975 | Dunlap et al. . |
| 4,004,398 | 1/1977 | Larsson et al. . |
| 4,374,491 | 2/1983 | Stortroen et al. . |
| 4,387,633 | 6/1983 | Ballantyne . |
| 4,400,313 | 8/1983 | Roberson et al. . |
| 4,455,931 | 6/1984 | Clifford et al. . |
| 4,552,720 | 11/1985 | Baker, Sr. et al. . |
| 4,860,958 | 8/1989 | Yerman . |
| 4,919,569 | 4/1990 | Wittenzelliner . |
| 4,934,283 | 6/1990 | Kydd . |
| 4,971,261 | 11/1990 | Solomons . |
| 4,980,090 | 12/1990 | Manchak, Jr. . |
| 5,005,496 | 4/1991 | Nagata . |
| 5,035,858 | 7/1991 | Held et al. . |
| 5,084,250 | 1/1992 | Hall . |
| 5,089,228 | 2/1992 | Meijer . |
| 5,124,126 | 6/1992 | Ripp . |
| 5,185,126 | 2/1993 | Adamski et al. . |

(List continued on next page.)

FOREIGN PATENT DOCUMENTS

| | | | |
|---|---|---|---|
| 0454122 | 10/1991 | European Pat. Off. ............. 100/92 |
| 519644 | 11/1957 | Italy ............................. 100/93 P |
| 52-46681 | 4/1977 | Japan ............................ 100/93 P |

*Primary Examiner*—Stephen F. Gerrity
*Attorney, Agent, or Firm*—Blakely Sokoloff Taylor & Zafman

[57] ABSTRACT

A system that sterilizes and compacts medical waste. The system includes a vessel which has a door that provides access to an inner chamber. The inner chamber is coupled to a compressor and a source of heating fluid. The vessel also has a jacket that surrounds the inner chamber. The jacket is coupled to the source of heating fluid and a source of cooling fluid. The operation of the system is controlled by a controller. To sterilize and compact medical waste, the door is initially opened and the waste is placed inside the inner chamber. The door is closed to seal the vessel. A vacuum is pulled within the inner chamber to remove any moisture contained therein. Simultaneous with the creation of the vacuum is the introduction of heating fluid to the jacket to heat the vessel. Heating fluid is then introduced to the inner chamber to sterilize the waste. After the waste is sterilized, a vacuum is pulled to remove the heating fluid from the inner chamber. The waste is then compacted by a piston. After the waste is compacted, a cooling water is introduced to the jacket to rapidly cool the vessel and the compacted waste. The door is then opened and the waste is removed from the inner chamber.

25 Claims, 4 Drawing Sheets

U.S. PATENT DOCUMENTS

| | | | |
|---|---|---|---|
| 5,207,994 | 5/1993 | Suzuki et al. | 100/93 P |
| 5,217,688 | 6/1993 | Von Lersner. | |
| 5,240,656 | 8/1993 | Scheeres. | |
| 5,252,290 | 10/1993 | Uesugi. | |
| 5,263,841 | 11/1993 | De Soet | 100/93 P |
| 5,277,869 | 1/1994 | Glazer et al. . | |
| 5,294,412 | 3/1994 | Orlando. | |
| 5,304,711 | 4/1994 | Tanaka et al. . | |
| 5,322,603 | 6/1994 | Kameda et al. . | |
| 5,336,843 | 8/1994 | Zimmer. | |
| 5,340,536 | 8/1994 | Datar et al. . | |
| 5,348,704 | 9/1994 | Tanaka. | |
| 5,355,789 | 10/1994 | Suzuki et al. | 100/92 |
| 5,362,443 | 11/1994 | Tanaka et al. . | |
| 5,364,589 | 11/1994 | Buehler et al. . | |
| 5,393,500 | 2/1995 | Kameda et al. . | |
| 5,401,444 | 3/1995 | Spinello. | |
| 5,489,200 | 2/1996 | McGraw et al. | 100/93 P |

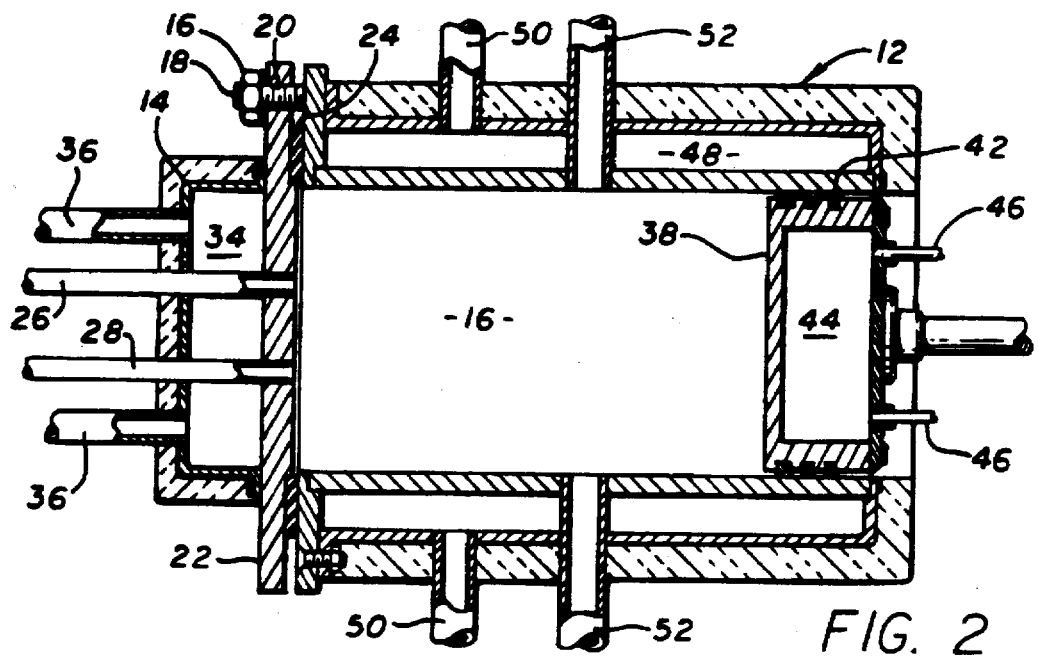
FIG. 2
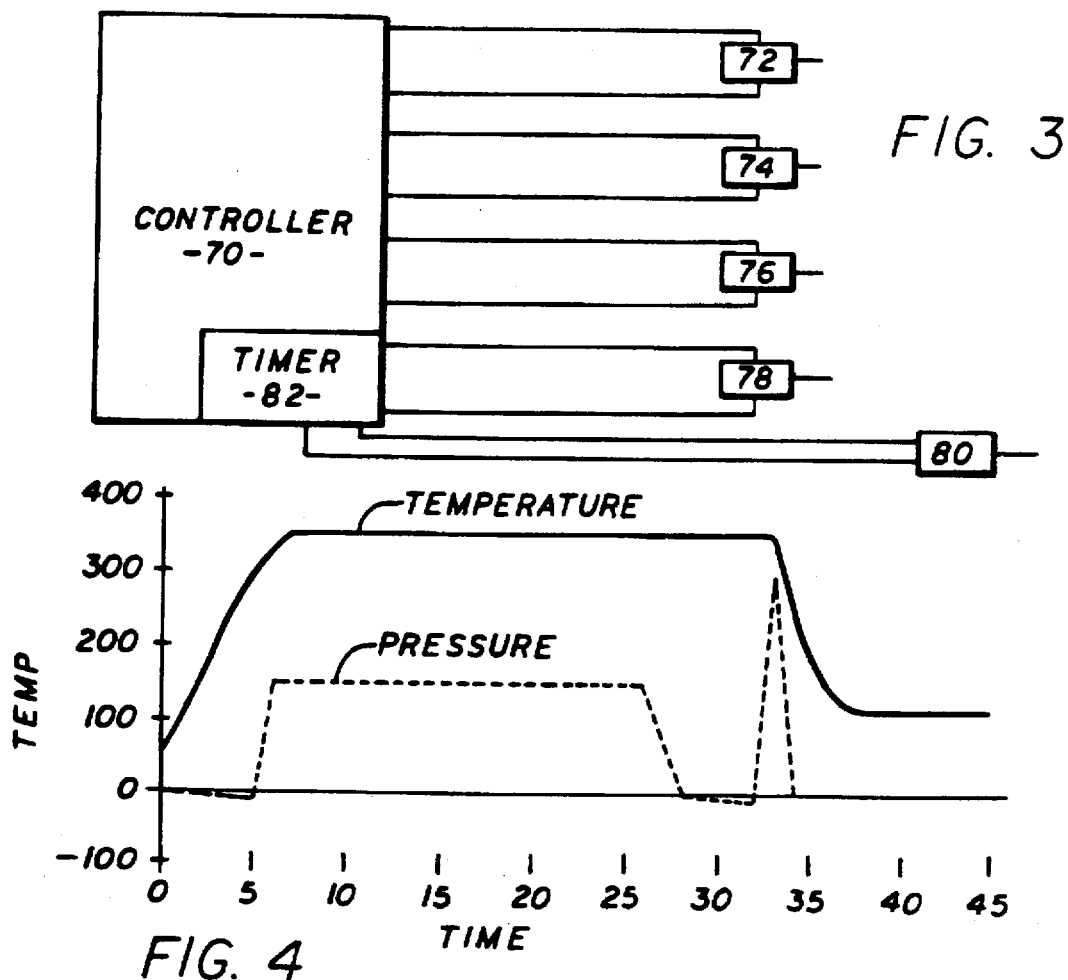
FIG. 3
FIG. 4

WASTE DISPOSAL SYSTEM WHICH INCLUDES A VESSEL WITH AN OUTER COOLING JACKET

This application is a continuation-in-part of Ser. No. 296,517 which was filed on Aug. 26, 1994 abandoned.

BACKGROUND OF THE INVENTION

1. Field of the Invention

The present invention relates to a system for sterilizing and compacting medical waste.

2. Description of Related Art

Medical waste can either be incinerated or placed within a landfill. Incineration is a relatively expensive and time consuming process. For this reason most medical waste is buried beneath the ground. To prevent contamination of the soil the waste is preferably sterilized before final disposal. Sterilization is typically accomplished by exposing the waste to an elevated temperature. The waste can also be shredded and compacted to reduce the bulk volume of the same.

U.S. Pat. No. 4,860,958 issued to Yerman discloses a device for the disposal of plastic syringes. The Yerman apparatus includes a cylinder which has a pair of heating plates that heat the syringes to a remolding temperature. Once the syringes reach a desired elevated temperature a piston compacts the waste into a solid block. The compacted heated waste is allowed to cool and then removed from the cylinder. The heating plates of the Yennan device have a relatively large thermal capacitance. The large thermal capacitance increases the time interval required to heat and cool the waste. The long time intervals reduce the efficiency of sterilizing and disposing large amounts of waste.

U.S. Pat. No. 4,552,720 issued to Baker, Sr. et al. discloses an autoclave that sterilizes and compacts medical waste. The medical waste is placed in a vessel that has an inner plastic liner. Steam is introduced to the vessel to sterilize the waste. The steam is removed and the waste is compacted by a piston. The plastic liner encloses the waste and provides an outer protective shell. The waste is allowed to cool and then removed from the vessel. Although the use of steam provides an efficient manner for sterilizing the waste, the cooling period is still unacceptable when disposing relatively large amounts of waste. It would therefore be desirable to provide a system for the efficient sterilization and compaction of medical waste.

SUMMARY OF THE INVENTION

The present invention is a system that sterilizes and compacts medical waste. The system includes a vessel which has a door that provides access to an inner chamber. The inner chamber is coupled to a compressor and a source of heating fluid. The vessel also has a jacket that surrounds the inner chamber. The jacket is coupled to the source of heating fluid and a source of cooling fluid. The operation of the system is controlled by a controller. To sterilize and compact medical waste, the door is initially opened and the waste is placed inside the inner cheer. The door is closed to seal the vessel. A vacuum is pulled within the inner chamber to remove any moisture contained therein. Simultaneous with the creation of the vacuum is the introduction of heating fluid to the jacket to heat the vessel. Heating fluid is then introduced to the inner chamber to sterilize the waste. After the waste is sterilized, a vacuum is pulled to remove the heating fluid from the inner chamber. The waste is then compacted by a piston. After the waste is compacted, a cooling fluid is introduced to the jacket to rapidly cool the vessel and the compacted waste. The door is then opened and the waste is removed from the inner chamber.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 2 is a cross-sectional view of a vessel of the system;

FIG. 3 is a schematic showing the controls of the system;

FIG. 4 is a graph showing the pressure and temperature cycles of the process for sterilizing and compacting the medical waste;

DETAILED DESCRIPTION OF THE INVENTION

Figure 1:
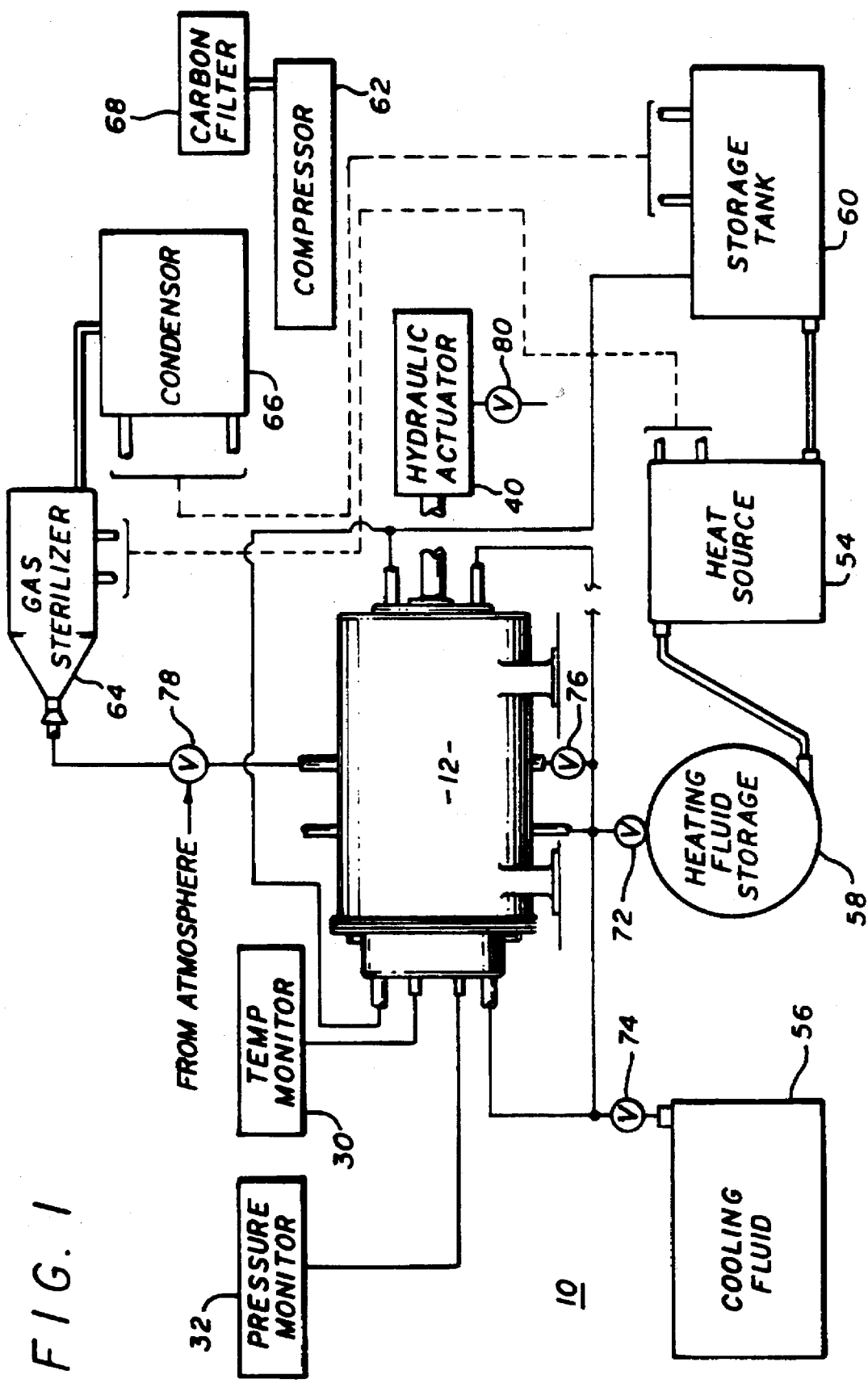
FIG. 1 is a schematic showing a medical waste disposal system of the present invention.

Referring to the drawings more particularly by reference numbers, FIGS. 1 and 2 show a medical waste disposal system 10 of the present invention. The system 10 includes a vessel 12 that can withstand relatively high pressures and temperatures. The vessel 12 has a door 14 that can provide access to an inner chamber 16. In the preferred embodiment, the inner chamber 16 has a diameter of 10 inches and a length of 16 inches.

To adequately seal the inner cheer 12, the door 14 may be pressed against the vessel 12 by a plurality of nuts 16 which screw onto a plurality of corresponding threaded studs 18. The studs 18 extend through a plurality of clearance holes 20 in an outer flange 22 of the door 14. A gasket 24 is preferably located between the outer flange 22 and the vessel 12 to seal the door 14. The door 14 may have a hinge to allow the door 14 to be easily opened and closed.

The door 14 may have a temperature passage 26 and a pressure passage 28 that are in fluid communication with the inner chamber 16 and coupled to a temperature monitor 30 and a pressure monitor 32, respectively. The monitors 28 and 30 monitor the temperature and pressure of the inner chamber 16. The door 14 may also have a jacket 34 which has a pair of openings 36.

Also located within the inner chamber 16 is a piston 38. The piston 38 is preferably coupled to an hydraulic actuator 40. The piston 38 may have a plurality of outer sealing rings 42. The piston 38 may also have a jacket 44 that has a pair of openings 46.

The vessel 12 may have a jacket 48 which surrounds the inner chamber 16. The jacket 48 has a plurality of openings 50. The inner chamber 16 may also have openings 52. In the preferred embodiment, the openings have a diameter of 0.75 inches.

Referring to FIG. 2, the jackets 34, 44 and 48 are coupled to a heat source 54 and a source of cooling fluid 56. The cooling fluid may be water from a municipal supply. The heat source 54 is also coupled to the inner chamber 16 through the openings 50 of the vessel 12. The heat source 54 provides heating fluid to the vessel 12. The system 10 may contain a heating fluid storage tank 58 to provide an available supply of heating fluid to the vessel 12. The heat source 54 may be further coupled to a cooling fluid storage tank 60. The heating fluid may be steam.

The inner chamber 16 is also coupled to a compressor 62. In line with the compressor 62 is a gas sterilizer 64 which sterilizes any matter removed from the inner chamber 16. The gas sterilizer 64 is typically coupled to the heat source 54. The heat source 54 provides heat to elevate the temperature of the matter that passes through the sterilizer 64 from the inner chamber 16 of the vessel 12. The heating fluid provided by the heat source 54 can be condensed by condenser 66 and return to the water storage tank 60. The matter removed from the inner chamber 16 is pumped to an activated charcoal filter 68 which removes any halogens before being vented to the atmosphere.

As shown in FIG. 3, the system is controlled by a controller 70. The controller 70 receives input signals from the temperature 30 and pressure 32 monitors and provides output signals to valves 72–80. Valve 72 controls the flow of heating fluid out of the heating fluid storage tank 58. Valve 74 controls the flow of cooling water out of the source of cooling fluid 56. Valve 76 controls the flow of heating fluid into the inner chamber 16. Valve 78 controls the flow of matter out of the inner chamber 16 and to the compressor 62. The valve 80 controls the movement of the actuator 40 and piston 38. The controller 70 may contain a timer 82 which provides a time value that is used by the controller 70 to sequence the system.

Figure 5:
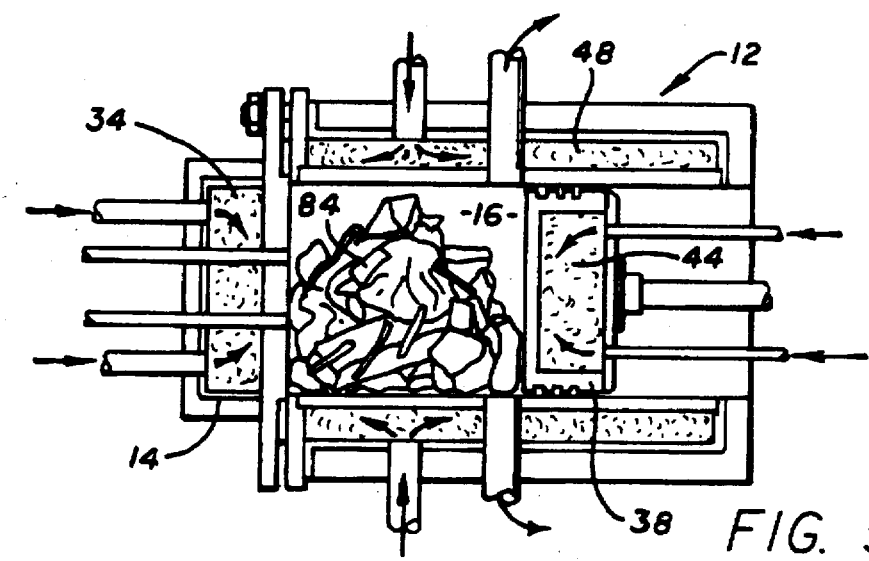
FIG. 5 is a cross-sectional view of the vessel showing a vacuum being created within an inner chamber and steam being introduced to an outer jacket.

FIGS. 5–10 and the graph of FIG. 4 show the operation of the system 10. The door 14 is initially opened and medical waste 84 is placed into the inner chamber 16. As shown in FIG. 5, the door 14 is closed and the controller 70 provides output signals to allow the compressor 62 to pull a vacuum in the inner chamber 16 and to introduce heating fluid into the jackets 34, 44 and 48 from the heating fluid tank 58. The piston 38 may also be moved to reduce the volume of the inner chamber 16. As shown in the graph of FIG. 4, the steam preferably heats the vessel to a temperature of at least 300° F. and creates a vacuum of at least 2.5 psia. The vacuum removes any moisture that may exist in the medical waste 84 and inner chamber 16.

Figure 6:
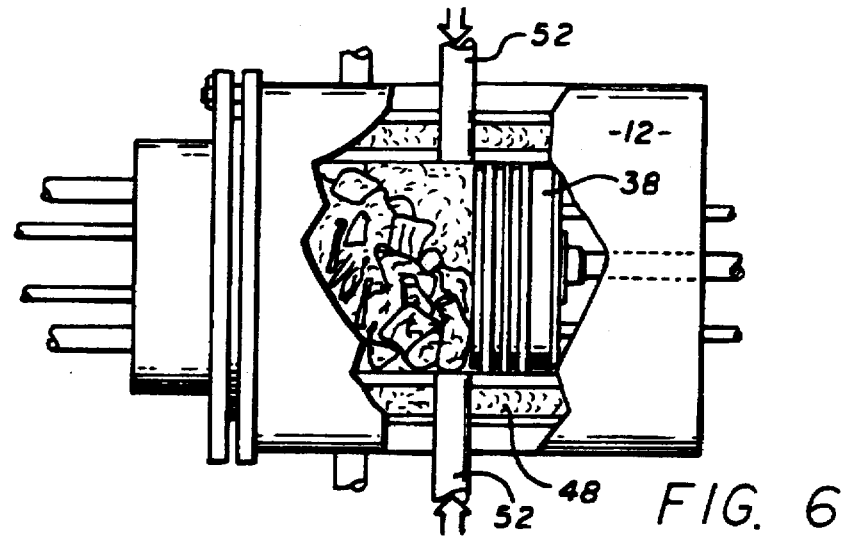
FIG. 6 is a cross-sectional view of the vessel showing heating fluid being introduced to the inner chamber.

When the vessel 12 reaches preset temperature and pressure conditions, or if the timer 82 reaches a predetermined time value (preferably 5 minutes), the controller 70 will switch the valves to introduce heating fluid into the inner chamber 16 as shown in FIG. 6. The controller 70 may also switch conditions when the change in pressure divided by the change in temperature (dP/dT) is approximately zero.

The configuration of the openings 52 and the pressure of the heating fluid is preferably such that the heating fluid is introduced into the inner chamber 16 at a hypersonic or supersonic velocity. The high velocity heating fluid being emitted by the nozzle openings 52 will tend to shred the medical waste, thereby improving the efficiency of sterilizing and compacting the waste. The openings 52 may be oriented to create either tangential or direct impingement nozzles.

As shown in the graph of FIG. 4, the heating fluid is introduced to the inner chamber 16 preferably until the chamber temperature and pressure have reached 350° F. and 150 psia, respectively, or the timer 82 has reached a predetermined value (preferably 5 minutes). The heating fluid is discontinued and the inner chamber is maintained in the heated pressurized state for a predetermined time period to sterilize the medical waste. In the preferred embodiment, the temperature and pressure are maintained for approximately 5 minutes. The medical waste typically contains a number of plastic products such as syringes, aprons, etc. The elevated temperatures and pressures tend to soften the plastic material to a state that allows for the compaction of the waste. If the medical waste contains an insufficient amount of plastic material, a volume of plastic material may be placed within the inner chamber to facilitate the compaction of the waste.

Figure 7:
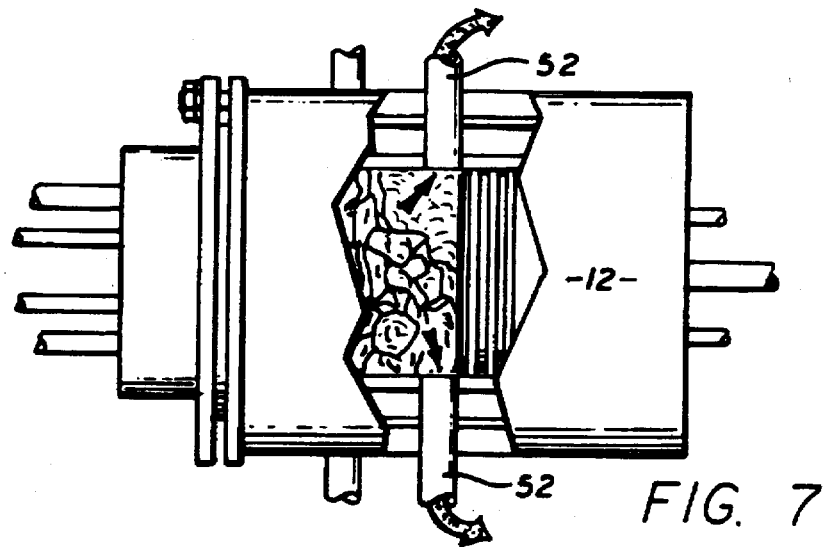
FIG. 7 is a cross-sectional view of the vessel showing heating fluid being removed from the inner chamber.

As shown in FIG. 7, after the waste is sterilized, the controller 70 switches the valves to allow the compressor 62 to remove the heating fluid from the inner chamber 16. As shown in the graph of FIG. 4, the pressure of the inner chamber 16 is typically reduced to approximately 2.5 psia.

Figure 8:
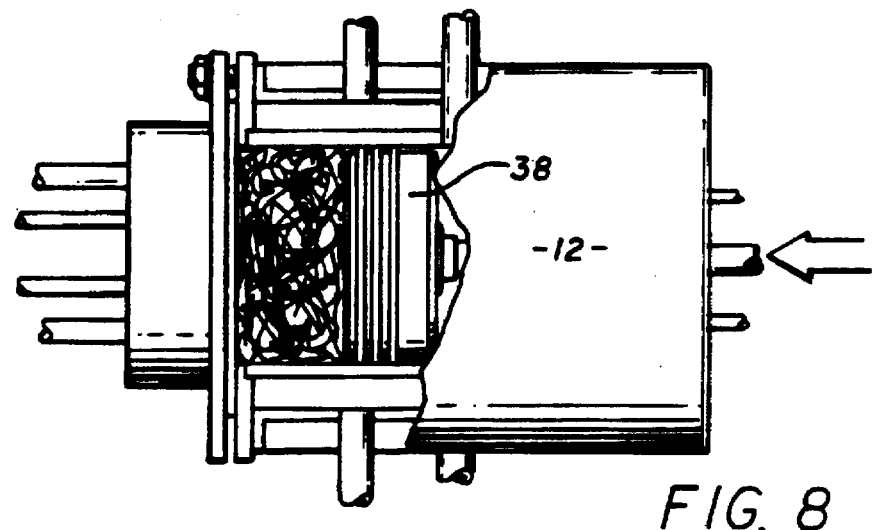
FIG. 8 is a cross-sectional view of the vessel showing the medical waste being compacted by a piston.
Figure 9:
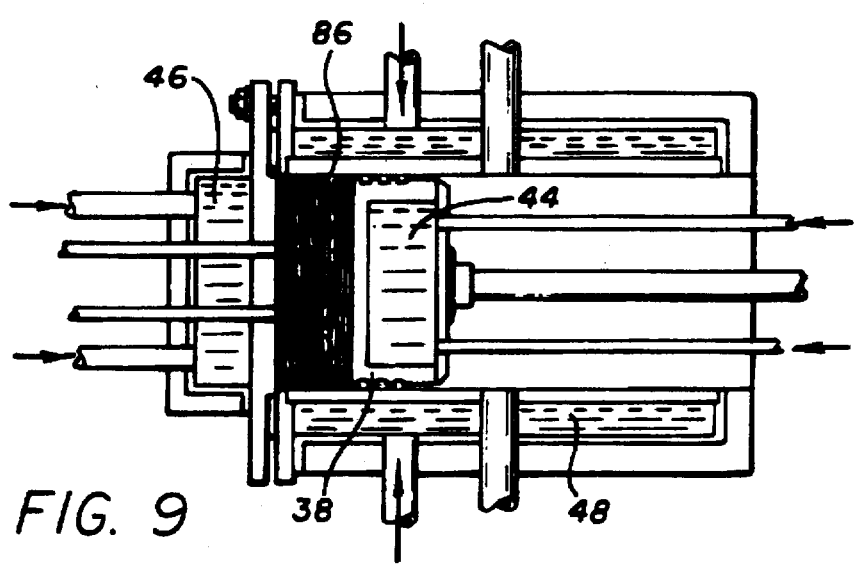
FIG. 9 is a cross-sectional view of the vessel showing a cooling fluid being introduced to the jacket to cool the vessel and the medical waste.

As shown in FIG. 8, the controller 70 then actuates the valve 80 to the hydraulic actuator 40 to move the piston 38 to compact the waste into a block 86. The softened plastic material creates a binder for the various waste products. The piston 38 typically compacts the waste to a pressure of 150 psia. As shown in FIG. 9, the controller 70 switches the valves to introduce cooling fluid into the jackets 34, 44 and 48. The cooling fluid reduces the temperature of the vessel and the compacted waste. The valve(s) 78 is also actuated to vent the inner chamber on the rear side of the piston 38. The compacted waste is typically allowed to cool for approximately 10 minutes to a condition where the inner chamber 16 is approximately 120° F.

Figure 10:
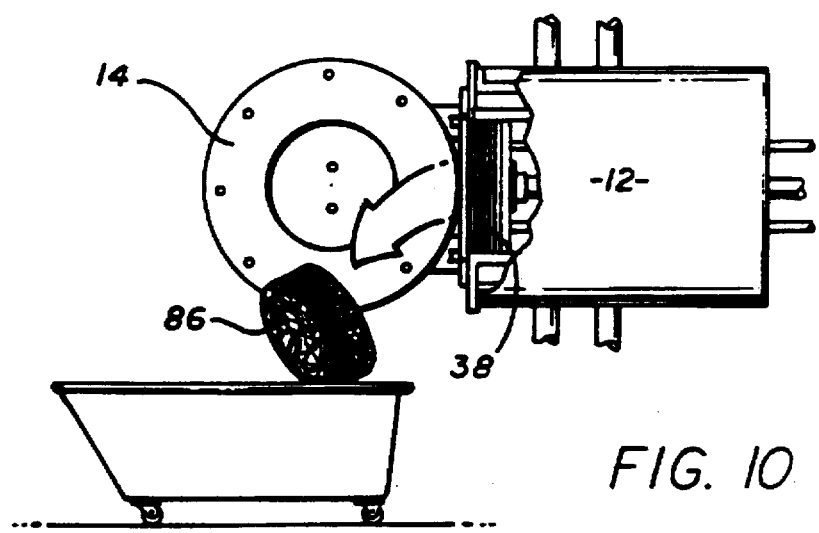
FIG. 10 is a cross-sectional view of the vessel showing the door opened and the compacted, sterilized, medical waste being removed from the inner chamber.

As shown in FIG. 10, the door 14 is then opened and the piston 38 pushes the sterilized and compacted waste 84 onto a cart 86. It is believed that the system of the present invention can sterilize and compact medical waste at a high rate, thereby providing a system that can efficiently dispose of a relatively large amount of waste.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A system for the disposal of medical waste, comprising:
   a vessel which has an inner chamber and an outer jacket;
   a door that provides access to said inner chamber and allows medical waste to be placed into said inner chamber;
   a heating system that heats the medical waste within said inner chamber, said heating system having a source of heating fluid that is in fluid communication with said outer jacket;
   a piston which compacts the medical waste within said inner chamber; and,
   a source of cooling fluid that is in fluid communication with said outer jacket so that a cooling fluid flows through said outer jacket and cools the compacted medical waste within said inner chamber.

2. The system as recited in claim 1 wherein said heating system includes a source of heating fluid that is in fluid communication with said inner chamber.

3. The system as recited in claim 2, wherein said heating fluid is introduced to said inner chamber through a nozzle.

4. The system as recited in claim 2, wherein said heating fluid is at a temperature of approximately 350° F.

5. The system as recited in claim 4, wherein said heating fluid is at a pressure of approximately 150 psi.

6. The system as recited in claim 1, wherein said piston has a jacket that is in fluid communication with a source of heating fluid and said source of cooling fluid.

7. The system as recited in claim 1, wherein said door has a jacket that is in fluid communication with a source of heating fluid and said source of cooling fluid.

8. The system as recited in claim 1, further comprising a compressor that is in fluid communication with said inner chamber to create a vacuum.

9. The system as recited in claim 8, further comprising a controller that is connected to said heating system, said source of cooling fluid, said piston and said compressor, wherein said controller causes said heating system to initially heat said vessel and said compressor to create a vacuum in said inner chamber, then causes said heating system to directly heat the medical waste, then causes said piston to compact the medical waste, and then causes said cooling system to cool said vessel.

10. A system for the disposal of medical waste, comprising:

a vessel which has an inner chamber and a jacket that surrounds said inner chamber;

a door that provides access to said inner chamber and allows the medical waste to be placed into said inner chamber;

a compressor that is in fluid communication with said inner chamber to create a vacuum in said inner chamber;

a source of heating fluid that is in fluid communication with said inner chamber and said jacket;

a piston which compacts the medical waste within said inner chamber; and, a source of cooling fluid that is coupled to said jacket.

11. The system as recited in claim 10, further comprising a controller that is connected to said source of heating fluid, said source of cooling fluid, said piston and said compressor, wherein said controller causes said source of heating fluid to initially heat said vessel and said compressor to create a vacuum in said inner chamber, then causes said source of heating fluid to apply heating fluid to said inner chamber, then causes said piston to compact the medical waste, and then causes said source of cooling fluid to cool said vessel.

12. The system as recited in claim 11, wherein said piston has a jacket in fluid communication with said source of heating fluid and said source of cooling fluid.

13. The system as recited in claim 12, wherein said door has a jacket in fluid communication with said source of heating fluid and said source of cooling fluid.

14. The system as recited in claim 13, wherein said heating fluid is introduced to said inner chamber through a nozzle.

15. The system as recited in claim 14, wherein said heating fluid is at a temperature of approximately 350° F.

16. The system as recited in claim 15, wherein said heating fluid is at a pressure of approximately 150 psi.

17. A system for the disposal of medical waste, comprising:

a vessel which has an inner chamber;

a door that provides access to said inner chamber and allows medical waste to be placed into said inner chamber;

a source of heating fluid that is in fluid communication with said inner chamber;

a nozzle that introduces the heating fluid into said inner chamber at a velocity that shreds the medical waste; and, a piston which compacts the medical waste within said inner chamber.

18. The system as recited in claim 17, further comprising a source of cooling fluid that is in fluid communication with a jacket that surrounds said inner chamber.

19. The system as recited in claim 18, wherein said source of heating fluid is in fluid communication with said jacket that surrounds said inner chamber.

20. The system as recited in claim 19, wherein said piston has a jacket that is in fluid communication with said source of heating fluid and said source of cooling fluid.

21. The system as recited in claim 20, wherein said door has a jacket that is in fluid communication with said source of heating fluid and said source of cooling fluid.

22. The system as recited in claim 21, further comprising a compressor that is in fluid communication with said inner chamber to create a vacuum within said inner chamber.

23. The system as recited in claim 22, further comprising a controller that is connected to said source of heating fluid, said source of cooling fluid, said piston and said compressor, wherein said controller causes said source of heating fluid to initially heat said vessel and said compressor to create a vacuum in said inner chamber, then causes said source of heating fluid to apply heating fluid to said inner chamber, and then causes said piston to compact the medical waste, and then causes said source of cooling fluid to cool said vessel.

24. The system as recited in claim 23, wherein said heating fluid is at a temperature of approximately 350° F.

25. The system as recited in claim 24, wherein said heating fluid is at a pressure of approximately 150 psi.

* * * * *